United States Patent
Kasahara (10) Patent No.: US 11,666,303 B2
(45) Date of Patent: Jun. 6, 2023

(54) ULTRASOUND DIAGNOSTIC APPARATUS, AND UMBILICAL CORD LENGTH MEASUREMENT METHOD

(71) Applicant: Hitachi, Ltd., Tokyo (JP)

(72) Inventor: Eiji Kasahara, Tokyo (JP)

(73) Assignee: FUJIFILM HEALTHCARE CORPORATION, Chiba (JP)

( * ) Notice: Subject to any disclaimer, the term of this patent is extended or adjusted under 35 U.S.C. 154(b) by 241 days.

(21) Appl. No.: 17/170,712

(22) Filed: Feb. 8, 2021

(65) Prior Publication Data

US 2021/0338191 A1 Nov. 4, 2021

(30) Foreign Application Priority Data

Apr. 30, 2020 (JP) .............................. JP2020-080111

(51) Int. Cl.
*A61B 8/06* (2006.01)
*A61B 8/08* (2006.01)
*A61B 8/02* (2006.01)

(52) U.S. Cl.
CPC .................. *A61B 8/06* (2013.01); *A61B 8/02* (2013.01); *A61B 8/488* (2013.01)

(58) Field of Classification Search
None
See application file for complete search history.

(56) References Cited

U.S. PATENT DOCUMENTS

| | | | |
|---|---|---|---|
| 5,749,831 A * | 5/1998 | Baker | A61B 8/02 600/455 |
| 2017/0143309 A1* | 5/2017 | Seki | G16H 50/30 |
| 2021/0106305 A1* | 4/2021 | Wang | A61B 8/463 |

FOREIGN PATENT DOCUMENTS

JP 06-261898 A 9/1994

* cited by examiner

*Primary Examiner* — Jonathan Cwern
(74) *Attorney, Agent, or Firm* — Mattingly & Malur, PC (57) ABSTRACT

A first region of interest and a second region of interest are set respectively including a first end and a second end of a blood vessel of interest running in an umbilical cord. A template representing a fluctuation of a pulse at the first end is produced from a change of brightness information in the first region of interest. A graph representing a fluctuation of a pulse at the second end is produced from a change of brightness information in the second region of interest. A propagation time of blood is calculated by identifying a portion, in the graph, which matches the template. A length of the umbilical cord is estimated based on the propagation time.

11 Claims, 8 Drawing Sheets

ULTRASOUND DIAGNOSTIC APPARATUS, AND UMBILICAL CORD LENGTH MEASUREMENT METHOD

CROSS REFERENCE TO RELATED APPLICATION

This application claims priority to Japanese Patent Application No. 2020-080111 filed on Apr. 30, 2020, which is incorporated herein by reference in its entirety including the specification, claims, drawings, and abstract.

TECHNICAL FIELD

The present disclosure relates to an ultrasound diagnostic apparatus, and to a method of measuring a length of an umbilical cord, and in particular to a technique for observing a pulse of a blood vessel.

BACKGROUND

Ultrasound diagnostic apparatuses are used in various medical fields. The ultrasound diagnostic apparatus is an apparatus which forms an ultrasonic image based on data acquired by transmitting and receiving ultrasound to and from a subject. In obstetrics, the ultrasonic inspection is executed in order to inspect the state of health of a mother or the state of growth of a fetus.

In the ultrasonic inspection in obstetrics, various measurements are taken. Currently, these measurements do not include measurement of the length of an umbilical cord. The umbilical cord is important tissue connecting the placenta and the fetus. When the umbilical cord is too long or is too short, problems tend to occur more frequently in the fetus and in the mother. Measuring the length of the umbilical cord during the ultrasonic inspection is desired, but currently, such a measurement is not realized. Similarly, for other tissues also, measuring the length of the tissue during the ultrasonic inspection is desired.

JP H6-261898 A discloses an ultrasound diagnostic apparatus which measures a pulse wave propagation velocity. In this ultrasound diagnostic apparatus, Doppler information is observed at two points on a blood vessel, and a pulse wave propagation time is calculated based on the acquired Doppler information. The pulse wave propagation velocity is then calculated by dividing a distance between the two points by the pulse wave propagation time. The distance between the two points is information which is known.

As described, measurement of a length of a tissue of interest during ultrasonic inspection is desired. The length of the tissue of interest can be calculated by multiplying an average velocity of blood flowing in a blood vessel of interest running in the tissue of interest by a time (time difference) of movement of blood between respective ends of the blood vessel of interest. In this case, a configuration may be considered in which the time difference is identified by comparing a blood velocity distribution or a Doppler waveform between the ends of the blood vessel of interest. However, because the blood velocity distribution and the Doppler waveform are information which change instantly and drastically, identifying the time difference in the above-described manner is not realistic.

An advantage of the present disclosure lies in measuring a length of a tissue of interest using ultrasound diagnosis. Alternatively, an advantage of the present disclosure lies in realizing a novel method of accurately measuring a propagation time of the blood. Further alternatively, an advantage of the present disclosure lies in realization of a novel technique for measuring a length of an umbilical cord.

SUMMARY

According to one aspect of the present disclosure, there is provided an ultrasound diagnostic apparatus comprising: a template producer that produces, based on data acquired by transmission and reception of ultrasound, a template which represents a fluctuation of a pulse at a first end of a blood vessel of interest running in a tissue of interest; a graph producer that produces, based on the data, a graph which represents a fluctuation of a pulse at a second end of the blood vessel of interest; a calculator that calculates a propagation time of blood between the first end and the second end by identifying a portion, in the graph, which matches the template; and an estimator that estimates a length of the tissue of interest based on the propagation time of the blood.

According to another aspect of the present disclosure, there is provided a method of measuring a length of an umbilical cord, the method comprising: producing, based on data acquired by transmission and reception of ultrasound, a template which represents a fluctuation of a pulse at an upstream-side end of a blood vessel of interest running in an umbilical cord; producing, based on the data, a graph which represents a fluctuation of a pulse at a downstream-side end of the blood vessel of interest; calculating a propagation time of blood from the upstream-side end to the downstream-side end by comparing the template against the graph; and estimating a length of the umbilical cord based on the propagation time of the blood.

According to another aspect of the present disclosure, there is provided a program executed by an information processor, which, when executed, causes the information processor to realize the functions of: producing, based on data acquired by transmission and reception of ultrasound to and from a mother, a template which represents a change with respect to time of an upstream-side end of a blood vessel of interest running in an umbilical cord; producing, based on the data, a graph which represents a change with respect to time of a downstream-side end of the blood vessel of interest; and calculating a propagation time of blood from the upstream-side end to the downstream-side end by identifying a portion, in the graph, which matches the template.

BRIEF DESCRIPTION OF DRAWINGS

Embodiment(s) of the present disclosure will be described based on the following figures, wherein.

DESCRIPTION OF EMBODIMENTS

An embodiment of the present disclosure will now be described with reference to the drawings.

(1) Overview of Embodiment

An ultrasound diagnostic apparatus according to an embodiment of the present disclosure comprises a template producer, a graph producer, a calculator, and an estimator. The template producer produces, based on data acquired by transmission and reception of ultrasound, a template which represents a fluctuation of a pulse at a first end of a blood vessel of interest running in a tissue of interest. The graph producer produces, based on the data, a graph which represents a fluctuation of a pulse at a second end of the blood vessel of interest. The calculator calculates a propagation time of blood between the first end and the second end by identifying a portion, in the graph, which matches the template. The estimator estimates a length of the tissue of interest based on the propagation time of the blood.

The fluctuation of the pulse is a change with respect to time of a pulse period (may also be called a pulse rate), and is a change of a long period and is gradual with respect to time, unlike the bloodstream velocity distribution and the Doppler waveform, which change intensely with respect to time. Thus, by comparing with each other the template and the graph which represent fluctuations of the pulse at two ends, it becomes possible to relatively accurately calculate a propagation time of the blood flowing between the two ends. According to the above-described configuration, the length of the tissue of interest can be estimated, and precision of the estimation can be improved.

The ends to be measured are set within the tissue of interest or within another tissue continuous from the tissue of interest. In cases in which a spatial deviation is caused between the end of the tissue of interest and the end of the blood vessel of interest, the length of the tissue of interest may be corrected to resolve the deviation. In some cases, when the deviation is small, the deviation may be ignored.

In another configuration of the present disclosure, the tissue of interest is an umbilical cord, and the estimator estimates a length of the umbilical cord as the length of the tissue of interest. Two arteries and one vein run within the umbilical cord. For the bloodstream flowing in these blood vessels, a phenomenon can be observed in which the pulse period changes with time in a relatively long period (for example, a period of a few seconds). Such a phenomenon is reflected in the template. In another configuration of the present disclosure, the blood vessel of interest to be measured is selected from among the three blood vessels. Alternatively, an individual measurement may be performed on each individual blood vessel, and the three measurement results acquired based thereon may be integrated.

In another configuration of the present disclosure, the estimator estimates the length of the tissue of interest by multiplying the propagation time of the blood by an average velocity of the blood. In another configuration of the present disclosure, the ultrasound diagnostic apparatus further comprises a velocity calculator that calculates the average velocity of the blood based on Doppler information included in the data. For the calculation of the average velocity, various methods may be employed. Alternatively, the calculated velocity may be corrected based on an angle between an ultrasonic beam and a direction of flow of the blood.

In another configuration of the present disclosure, the average velocity of the blood is designated by a user or is identified based on fetus information. According to this configuration, the average velocity can be identified without the use of an ultrasonic Doppler method; that is, without increasing an amount of irradiation of the ultrasound to the fetus. For example, the average velocity may be designated by the user based on a measurement result from the past. Alternatively, the average velocity may be automatically identified based on the weeks of pregnancy.

In another configuration of the present disclosure, the ultrasound diagnostic apparatus further comprises an image former that forms an ultrasonic image based on the data. The template producer produces the template based on a change with respect to time of brightness information at the first end in the ultrasonic image. The graph producer produces the graph based on a change with respect to time of brightness information at the second end in the ultrasonic image.

The brightness information of the blood vessel (and portions therein and outside thereof) changes with the pulse of the blood vessel. In the above-described configuration, such a change with respect to time of the brightness information is utilized to produce the template and the graph. Alternatively, other information may be utilized such as a change of a diameter of the blood vessel and a displacement of a tracking point in the blood vessel.

In another configuration of the present disclosure, a first region of interest is set on the ultrasonic image, including the first end and for observing the change with respect to time of the brightness information at the first end. In addition, a second region of interest is set on the ultrasonic image, including the second end and for observing the change with respect to time of the brightness information at the second end. The first region of interest and the second region of interest may be set by the user or may be automatically set by image analysis.

In another configuration of the present disclosure, two markers respectively indicating the first region of interest and the second region of interest are displayed on the ultrasonic image. In addition, the propagation time of the bloodstream and the length of the tissue of interest are displayed along with the ultrasound image.

A method of measuring a length of an umbilical cord according to an embodiment of the present disclosure comprises: a template producing step; a graph producing step; a calculating step; and an estimating step. In the template producing step, a template is produced, based on data acquired by transmission and reception of ultrasound, which represents a fluctuation of a pulse at an upstream-side end of a blood vessel of interest running in the umbilical cord. In the graph producing step, a graph is produced, based on the data, which represents a fluctuation of a pulse at a downstream-side end of the blood vessel of interest. In the calculating step, a propagation time of blood from the upstream-side end to the downstream-side end is calculated by comparing the template against the graph. In the estimating step, a length of the umbilical cord is estimated based on the propagation time of the blood.

In another configuration of the present disclosure, the blood vessel of interest is an artery. In this case, the upstream-side end is located inside or near a fetus, and the downstream-side end is located inside or near a placenta. Alternatively, the blood vessel of interest is a vein. In this case, the upstream-side end is located inside or near a placenta, and the downstream-side end is located inside or near a fetus.

A program according to an embodiment of the present disclosure is a program executed by an information processor, which, when executed, causes the information processor to realize: a template producing function; a graph producing function; and a calculating function. The template producing function is a function to produce, based on data acquired by transmission and reception of ultrasound to and from a mother, a template which represents a change with respect to time of an upstream-side end of a blood vessel of interest running in an umbilical cord. The graph producing function is a function to produce, based on the data, a graph which represents a change with respect to time of a downstream-side end of the blood vessel of interest. The calculating function is a function to calculate a propagation time of blood from the upstream-side end to the downstream-side end by identifying a portion, in the graph, which matches the template.

The program is installed to the information processor via a recording medium or via a network. As the recording medium, a recording medium which non-transitorily stores the program may be exemplified. The concept of the recording medium includes a transportable recording medium. The information processor is a device having a processor which executes a program, and the concept of the information processor includes an ultrasound diagnostic apparatus, an ultrasound diagnostic system, a computer, and the like.

(2) Detail of Embodiment

Figure 1:
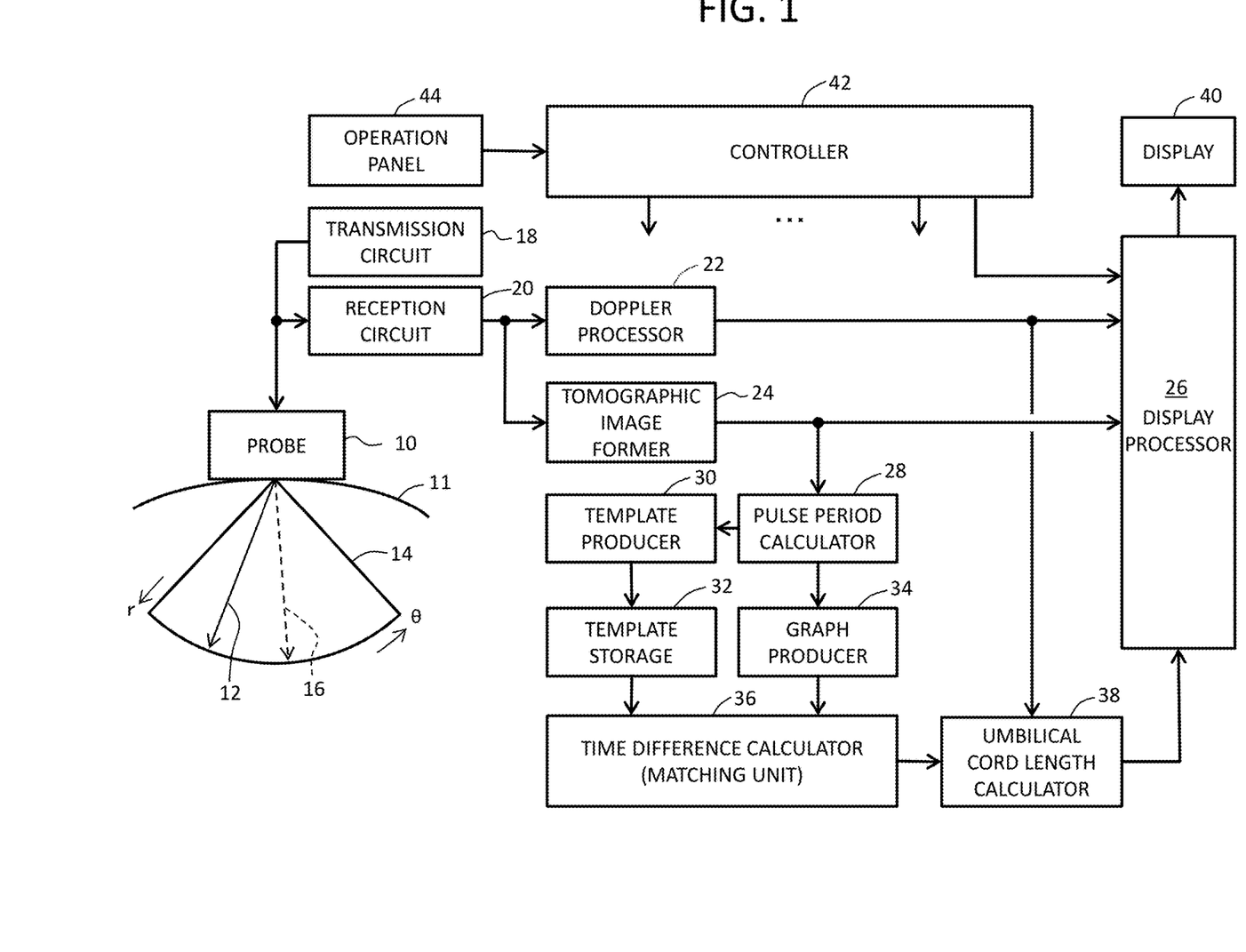
FIG. 1 is a block diagram showing an ultrasound diagnostic apparatus according to an embodiment of the present disclosure.

FIG. 1 shows an ultrasound diagnostic apparatus according to an embodiment of the present disclosure. The ultrasound diagnostic apparatus is an apparatus which is installed in a medical institution such as a hospital, and which forms and displays an ultrasonic image based on a reception signal acquired by transmission and reception of ultrasound to and from a subject. A structure and an operation of the ultrasound diagnostic apparatus will now be described assuming an ultrasonic inspection of pregnant women in obstetrics.

A probe 10 is a transportable transmission/reception device. The probe 10 is held by an inspector (a doctor, an inspection technician, or the like) who is a user. A transmission/reception surface of the probe 10 is caused to contact an abdominal surface of the mother (pregnant mother). The probe 10 includes a transducer array. The transducer array is formed from a plurality of transducers which are one-dimensionally arranged. An ultrasound beam 12 is formed by the transducer array, and is electronically scanned. With this process, a scanning plane 14 is formed. A position and an orientation of the probe 10 are adjusted by the inspector so that one or a plurality of observation sites in the fetus are included in the scanning plane 14.

As an electronic scanning method of the ultrasound beam 12, there can be exemplified an electronic linear scanning method, an electronic sector scanning method, and the like. A scanning plane S has a coordinate system which is identified by a depth direction r and a scanning direction θ. Alternatively, a two-dimensional transducer array may be provided in the probe 10. That is, volume data may be acquired from a three-dimensional space by two-dimensional scanning of the ultrasound beam.

When a B mode is selected, in which a tomographic image is displayed, the ultrasound beam 12 is electronically scanned as described above. When a PW mode (or a CW mode) is selected, in which Doppler information is observed, an ultrasound beam 16 is repeatedly formed in a particular observation direction. In the present embodiment, a composite mode is selected in which the B mode and the PW mode are executed in a time divisional manner as necessary.

A transition circuit 18 is an electronic circuit which functions as a transmission beam former. A reception circuit 20 is an electronic circuit which functions as a reception beam former. During transmission, a plurality of transmission signals are supplied in parallel to each other from the transmission circuit 18 to the transducer array. With this process, a transmission beam is formed. During reception, when a reflected wave from within a living body is received by the transducer array, a plurality of reception signals are output in parallel to each other from the plurality of transducer elements.

For the plurality of reception signals, at the reception circuit 20, phase alignment and summing (that is, delay and summing) is applied, so that beam data corresponding to the reception beam are produced. During execution of the B mode, one set of reception frame data is produced for each electronic scanning of the ultrasound beam 12 of one time. One set of reception frame data is formed from a plurality of beam data arranged in the scanning direction. One set of beam data is formed from a plurality of sets of echo data arranged in a depth direction. During execution of the PW mode, the ultrasound beam is repeatedly formed in a particular direction. During execution of the composite mode, for example, the transmission and reception of a plurality of times for the B mode and the transmission and reception of once for the PW mode are alternately executed.

Downstream of the reception circuit 20, a beam data processor is provided, which is not shown in the figures. A Doppler processor 22 is a circuit which extracts Doppler information from each set of beam data acquired by transmission and reception according to the PW mode. Specifically, information of a sample gate is taken out from each set of beam data, and, based on a frequency analysis of this information, a spectrum is produced which is a frequency analysis result of the Doppler information. Data indicating the spectrum are sent from the Doppler processor 22 to a display processor 26. In addition, these data are also sent to an umbilical cord length calculator 38. The umbilical cord length calculator 38 calculates an average velocity based on the spectrum. Alternatively, the calculation of the average velocity may be executed at the Doppler processor 22.

A tomographic image former 24 is a module which produces a display frame data array from a reception frame data array. The tomographic image former 24 has a digital scan converter (DSC). The DSC has a coordinate conversion function, an interpolation function, a frame rate adjustment function, or the like. Each set of produced display frame data corresponds to a tomographic image. Alternatively, other ultrasonic images may be formed such as a two-dimensional bloodstream image. Alternatively, the average velocity may be calculated from such other ultrasonic images. The display frame data array (that is, a tomographic image array in a time sequential order) is sent to the display processor 26 and a pulse period calculator 28.

The display processor 26 has an image combining function, a color calculation function, and the like. The data of the tomographic image are sent through the display processor 26 to a display 40. The display 40 is formed from an LCD, an organic EL device, or the like. On a screen of the display 40, a tomographic image is displayed as an ultrasonic image, and two markers showing two regions of interest, a propagation time of the blood, an estimated length of the umbilical cord, and the like are also displayed, as will be described later.

The ultrasound diagnostic apparatus according to the present embodiment comprises the pulse period calculator 28, a template producer 30, a template storage 32, a graph producer 34, a time difference calculator 36, and the umbilical cord length calculator 38. These structures correspond to, for example, a plurality of functions realized by a processor (which may be a CPU as will be described later). Before describing these structures, presumptions will be described.

With adjustment of a position and an orientation of the probe 10, a tomographic image including a fetus image and a placenta image is displayed. In this process, the position and the orientation of the probe 10 are adjusted such that two ends of the umbilical cord appear in the tomographic image; more specifically, a first end (an upstream-side end in the present embodiment) of a blood vessel of interest running in the umbilical cord and a second end (a downstream-side end in the present embodiment) of the blood vessel of interest appear in the tomographic image. Alternatively, so long as pattern matching to be described later can be executed, the position and the orientation of the probe 10 may be adjusted such that the ends successively appear in the tomographic image.

Two arteries and one vein run in the umbilical cord, and one of these blood vessels is selected by the user as a blood vessel of interest. Alternatively, the selection may be automated. The umbilical cord has a serpentine form in an amniotic fluid, and, normally, the tomographic image does not contain the entirety of the umbilical cord, and only a portion thereof appears on the tomographic image.

In the present embodiment, after the position and the orientation of the probe 10 are adjusted, a first region of interest (first ROI) is manually set on the tomographic image, surrounding the first end of the blood vessel of interest, and a second region of interest (second ROI) is manually set, surrounding the second end of the blood vessel of interest. Alternatively, the two regions of interest may be automatically set by an analysis of the tomographic image. A position, a size, a shape, and the like of each of the regions of interest are suitably determined so as not to include other blood vessels.

The pulse period calculator 28 successively calculates the pulse period from a change with respect to time of brightness information in each region of interest. As the pulse period, a number of pulses per unit time may be calculated. The ends of the blood vessel of interest expand and contract periodically on the tomographic image, or forms or positions of the ends change periodically. Thus, a corresponding portion periodically becomes brighter or darker. The pulse period at each individual time may be calculated from the change of the tomographic image. In the fetus, the period changes with respect to time in a significantly long period (for example, a period of 4.5 seconds), and thus, there is a fluctuation in the pulse. In some cases, such a fluctuation of a pulse may be observed for an adult.

The pulse period calculator 28 outputs to the graph producer 34 a period array calculated from the brightness information in the first region of interest to the template producer 30, and a period array calculated from the brightness information in the second region of interest.

The template producer 30 produces a template as the input period array or as a part of the input period array. In the present embodiment, the template is a waveform showing a change with respect to time of the pulse period over a certain period. For example, the certain period is set in a range of 1 second to 10 seconds. It should be noted that the numerical values described herein are merely exemplary, and are not limiting. The template produced from the brightness information at the first end is stored in the template storage 32.

The graph producer 34 produces a graph showing a change with respect to time of the pulse based on the period array produced from the brightness information at the second end. The graph is a waveform. The production of the template and the production of the graph are simultaneously executed. Alternatively, the productions of the template and the graph may be executed at separate timings, so long as the pattern matching to be described below can be appropriately executed.

The time difference calculator 36 functions as a matching unit. That is, of the graph that is produced, a portion that matches the template is identified. In this process, for example, while a template position is changed with respect to the graph, a correlation calculation is executed at each template position. Establishment of the match is decided when a correlation value satisfies a certain condition.

The time difference calculator 36 calculates a difference (time difference) between the time of production of the template and the time of establishment of matching. The time difference may also be called a template propagation time. That is, the time difference corresponds to a time of movement of the blood from the first end to the second end in the blood vessel of interest. The present embodiment takes advantage of the fact that the fluctuation of the pulse changes with a long period, and determines the propagation time of the blood by the pattern matching of the fluctuation between the ends.

The umbilical cord length calculator 38 multiplies the propagation time by an average velocity (average flow rate), to estimate the length of the umbilical cord. The average velocity is identified based on the Doppler information. Alternatively, the average velocity may be determined based on the weeks of pregnancy or the like. Alternatively, a table may be prepared which identifies the average velocity based on information such as the weeks of pregnancy. The Doppler information is normally acquired from the first end. Alternatively, the Doppler information may be acquired from the second end or from another site. Data indicating the length of the umbilical cord are sent to the display processor 26.

Alternatively, data showing the template or data showing the graph may be sent to the display processor 26. In other words, the template and the graph may be displayed on the screen of the display 40. In the present embodiment, along with the tomographic image which is a video image, the propagation time and the length of the umbilical cord which are measured in real time are displayed as numerical values.

A controller 42 controls operations of various structures shown in FIG. 1. The controller 42 is formed from, for example, a CPU which executes a program. An operation panel 44 is connected to the controller 42. The operation panel 44 is an input device having a plurality of buttons, a trackball, a keyboard, or the like. The two regions of interest and a sample gate are set using the operation panel 44. A start of acquisition of the template is instructed using the operation panel 44. The average velocity may be designated using the operation panel 44, or the weeks of pregnancy may be input using the operation panel 44.

Figure 2:
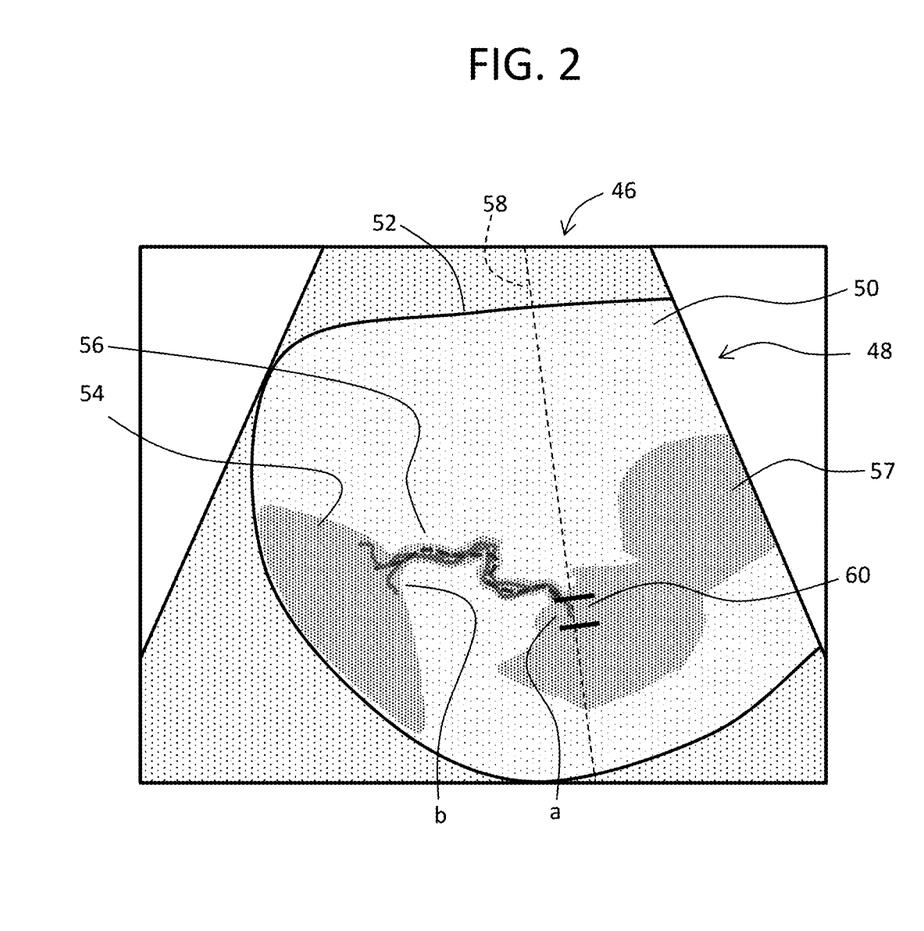
FIG. 2 is a diagram showing an upstream-side end (first end) and a downstream-side end (second end) of a blood vessel of interest.

FIG. 2 shows a tomographic image 46. FIG. 2 is a schematic diagram for explaining the present embodiment. In the example configuration illustrated in FIG. 2, a cross section 48 of a uterus appears in the tomographic image 46. Reference numeral 50 shows the amniotic fluid, and reference numeral 52 shows a uterine wall. A placenta 54 and a fetus 57 are connected to each other via an umbilical cord 56. The umbilical cord 56 includes two arteries and one vein, present in this order from the side of the fetus. Normally, the entirety of the umbilical cord 56 does not appear in the tomographic image 46, but in FIG. 2, the entirety of the umbilical cord 56 is schematically illustrated, for the understanding of the present embodiment.

In the example configuration illustrated in FIG. 2, the blood vessel of interest is a particular artery. An upstream-side end a of the artery serves as the first end which is a measurement target for template production, and a downstream-side end b of the artery serves as the second end which is a measurement target for graph production.

Based on an understanding that one-side end and the other-side end of the umbilical cord 56 extend respectively to an inside of the fetus 57 and to an inside of the placenta 54, the upstream-side end a belongs to the one-side end of the umbilical cord 56, and the downstream-side end b belongs to the other-side end of the umbilical cord 56. On the other hand, based on an understanding that the one-side end and the other-side end of the umbilical cord 56 do not extend to the inside of the fetus 57 and to the inside of the placenta 54, respectively, the upstream-side end a is located near the one-side end of the umbilical cord 56 and in the fetus 57, and the downstream-side end b is located near the other-side end of the umbilical cord 56 and in the placenta 54. Under either understanding, there is no significant difference in the length of the umbilical cord.

In FIG. 2, a direction 58 for observing Doppler information is set to pass through the upstream-side end a. On the direction 58, a sample gate 60 is set to include the upstream-side end a. The Doppler information is acquired from inside of the sample gate 60. The acquisition of the Doppler information may be performed before the template and the graph are produced, may be performed while the template and the graph are produced, or may be performed after the template and the graph are produced. When the average velocity is calculated from the Doppler information, a velocity correction may be applied according to an angle between a bloodstream direction and a beam direction.

Figure 3:
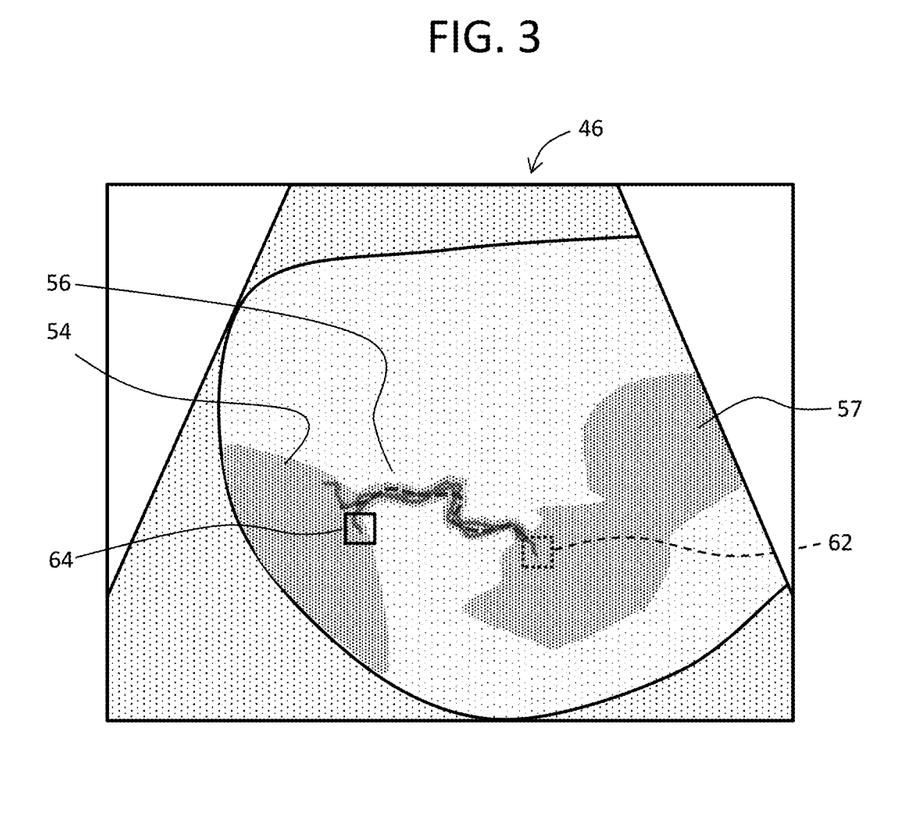
FIG. 3 is a diagram showing a first region of interest and a second region of interest.

FIG. 3 shows two regions of interest 62 and 64. On the tomographic image 46, the first region of interest 62 is set surrounding the upstream-side end, and the second region of interest 64 is set surrounding the downstream-side end. Elements identical to the elements which have already been described are assigned the same reference numerals, and their descriptions will not be repeated. This is also applicable for all drawings from FIG. 4 and on. Alternatively, of the setting of the first region of interest 62 and the setting of the sample gate, one of these settings may also function as the other setting.

Figure 4:
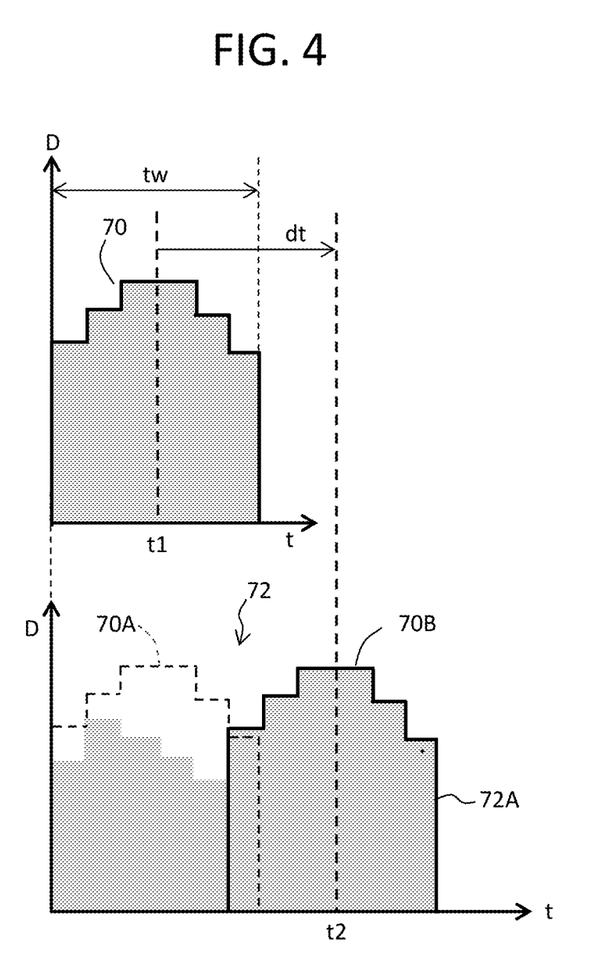
FIG. 4 is a diagram for explaining comparison of a template and a graph.

FIG. 4 shows a template 70 and a graph 72. A horizontal axis t is a time axis, and a vertical axis D shows a pulse period. The pulse period changes with a long period. That is, there is a fluctuation in the pulse period. A template period tw is set so that the entirety or a part of a period of the fluctuation is included in the template period. For example, as the template period tw, a period in a range of 0.5 seconds to 10 seconds may be designated. Alternatively, a period in a range of 2 seconds to 8 seconds may be designated. In the example configuration illustrated in FIG. 4, a center of the template period tw is shown by t1.

The graph 72 grows with time. At each timing, the template 70 is compared against the graph 72 (for example, refer to reference numeral 70A). For the comparison, a correlation calculation is executed. When a correlation value satisfies a certain condition, match is decided. In the example configuration illustrated in FIG. 4, in the graph 72, a portion shown by reference numeral 72A matches the template 70 (refer to reference numeral 70B). A center of the portion 72A is shown by reference numeral t2. A time difference dt from t1 to t2 can be regarded as the propagation time of the blood in the blood vessel of interest. The length of the blood vessel of interest can be estimated by multiplying the propagation time of the blood by the average velocity of the blood, and the length of the umbilical cord can be estimated by the length of the blood vessel of interest. In this process, various corrections may be applied as necessary.

Figure 5:
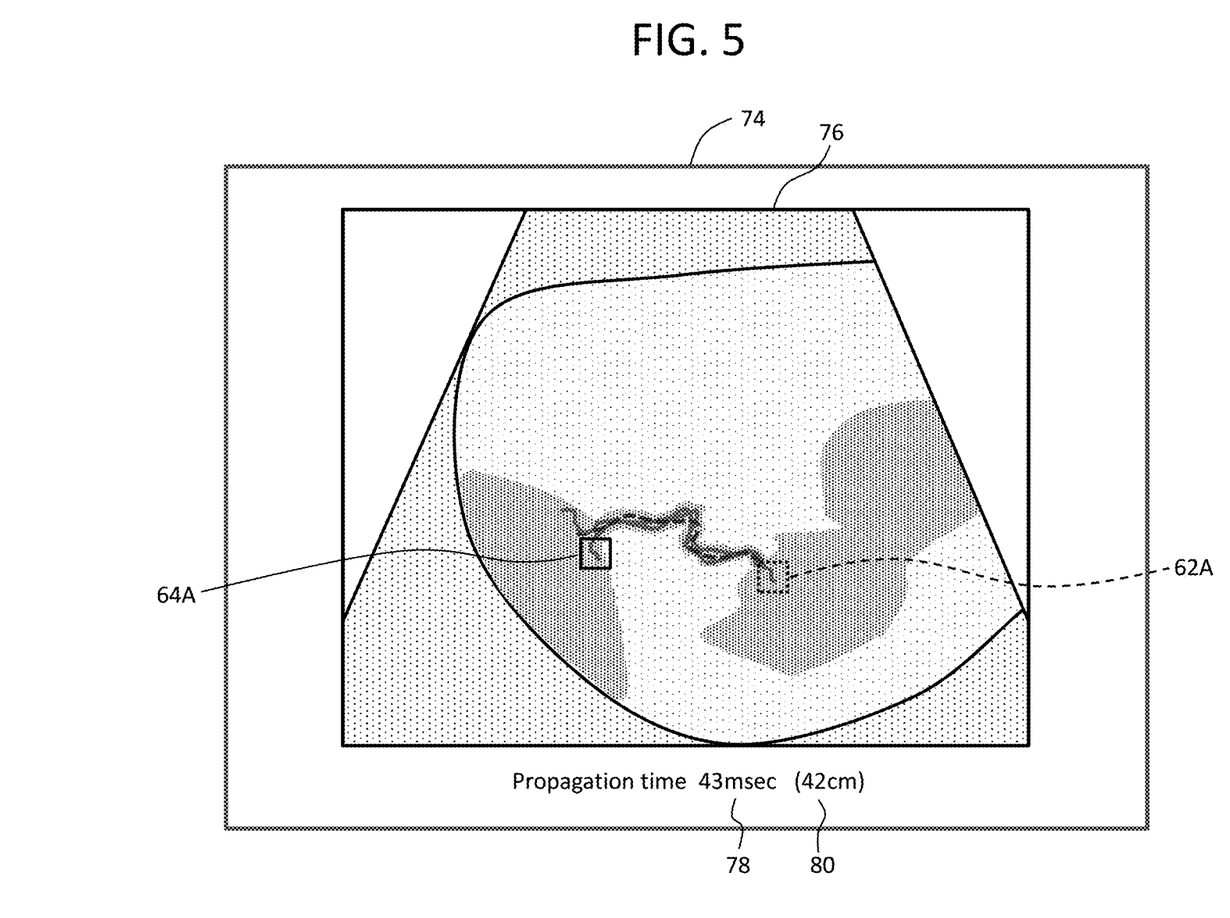
FIG. 5 is a diagram showing an example display of a measurement result.

FIG. 5 shows an example display. A tomographic image 76 is displayed in a screen 74. The tomographic image 76 includes a marker 62A showing the first region of interest which is set with regard to the first end, and a marker 64A showing the second region of interest which is set with regard to the second end. At a lower part of the tomographic image 76, a numerical value 78 showing the propagation time which is calculated and a numerical value indicating the estimated length of the umbilical cord are displayed. By referring to these numerical values, it becomes possible to diagnose an abnormality of the umbilical cord being too long or an abnormality of the umbilical cord being too short.

In the configuration described above, the artery is set as the observation target, but alternatively, a vein may be set as the observation target. In this case, the upstream-side end is set on the side of the placenta, and the downstream-side end is set on the side of the fetus.

Figure 6:
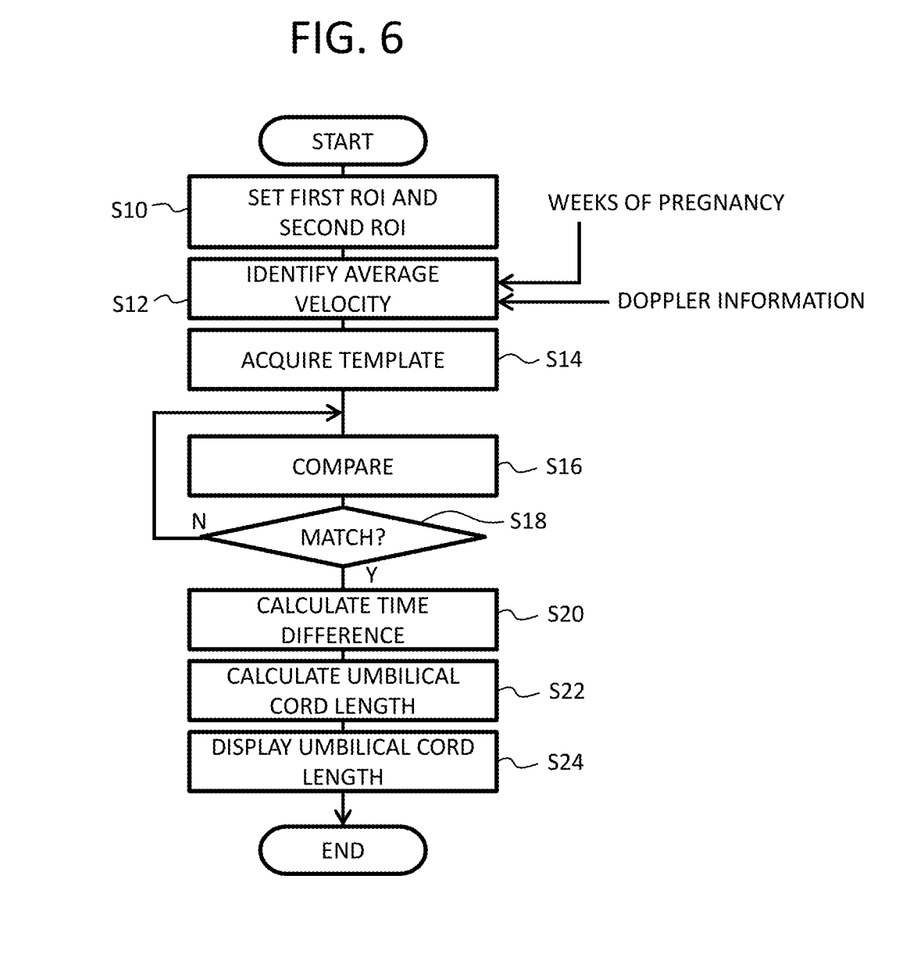
FIG. 6 is a flowchart showing an example operation.

FIG. 6 shows an example operation as a flowchart. In S10, the first region of interest (first ROI) and the second region of interest (second ROI) are set on the tomographic image, respectively including the first end and the second end of the blood vessel of interest. In S12, the average velocity of the blood is identified. In this process, the Doppler information may be utilized. Alternatively, the average velocity may be identified based on the weeks of pregnancy. In S14, the template is produced based on the brightness information in the first region of interest.

In S16, the template is successively compared against the graph, which is produced based on the brightness information in the second region of interest. The comparison is repeated until the match is decided in S18. When the match is decided, in S20, the time difference; that is, the propagation time, is calculated. In S22, the propagation time of the blood is multiplied by the average velocity of the blood, to estimate the length of the umbilical cord. In S24, the estimated length of the umbilical cord is displayed.

Alternatively, the lengths of the umbilical cord may be determined by a method similar to the above for two or three blood vessels in the umbilical cord, and an average value thereof may be calculated. Alternatively, the above-described method may be applied to a recorded tomographic image array. Alternatively, in place of the change of the brightness information, reference may be made to a change of a blood vessel diameter, a displacement of a tracking point, or the like. Alternatively, the length of the umbilical cord may be calculated by the above-described method based on volume data. In this case, a burden during the adjustment of the position and the orientation of the probe can be reduced, and the first region of interest and the second region of interest can be set more appropriately. Alternatively, a similar method may be applied to other tissues including a blood vessel.

Figure 7:
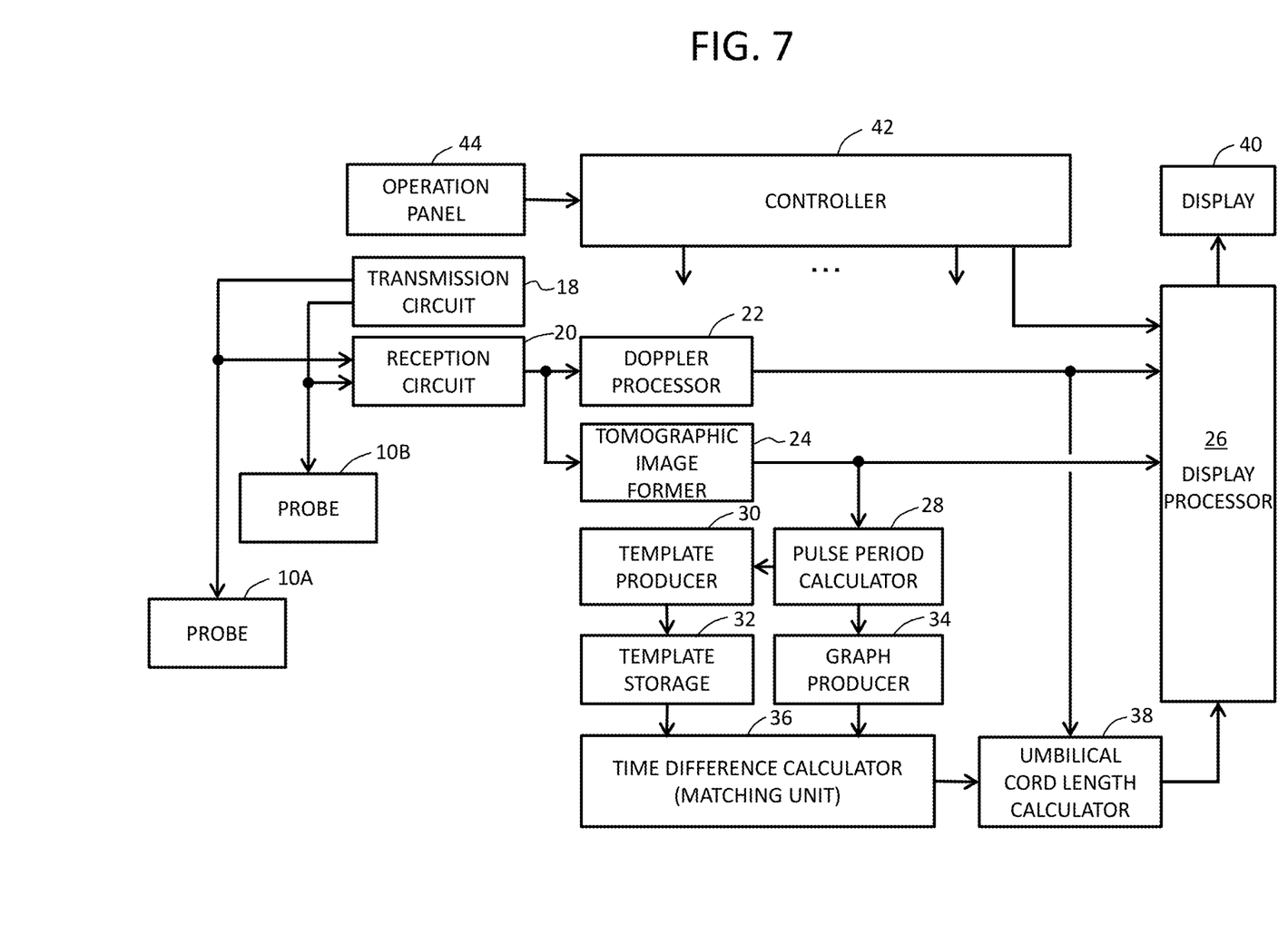
FIG. 7 is a block diagram showing an ultrasound diagnostic apparatus according to an alternative configuration.

FIG. 7 shows an alternative configuration. To the transmission circuit 18 and the reception circuit 20, two probes 10A and 10B which operate simultaneously are connected.

For example, the first end of the blood vessel of interest is observed by the probe 10A, and the second end of the blood vessel of interest is observed by the probe 10B. When the structure shown in FIG. 7 is employed, two transmission systems which operate in parallel to each other and two reception systems which operate in parallel to each other may be provided, or one transmission system and one reception system may be respectively operated in a time divisional manner.

Figure 8:
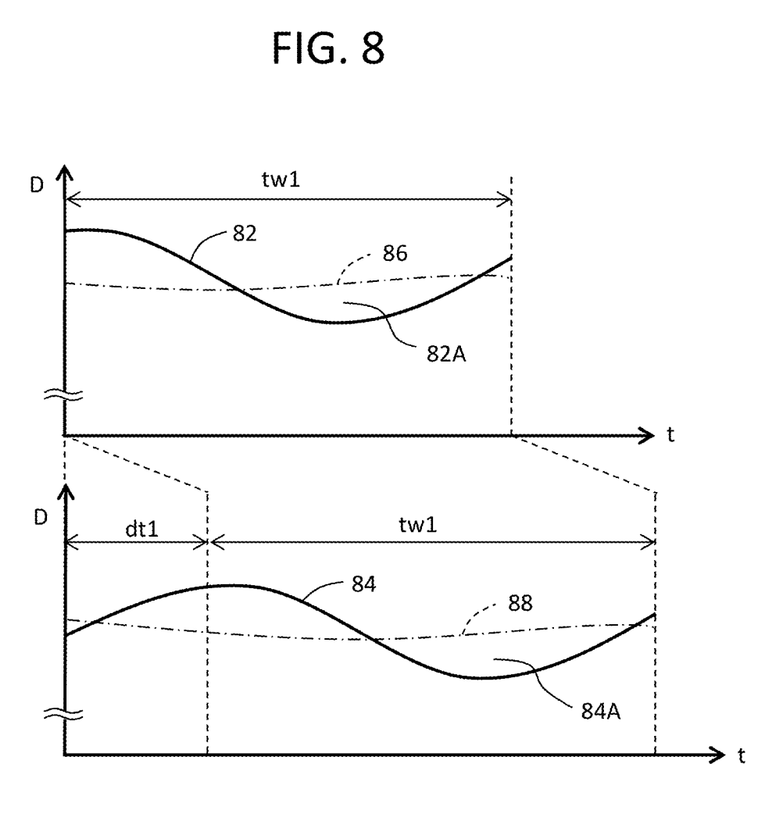
FIG. 8 is a diagram showing another method of comparing a template and a graph.

FIG. 8 shows another method of matching. An averaging process is applied to a waveform 82 showing the fluctuation of the pulse period at the first end, to produce an average curve 86. A difference 82A between the average curve 86 and the waveform 82 forms a template. The difference 82A is a fluctuation component which is taken into consideration in the present embodiment. The template period is shown by tw1.

In addition, an averaging process is similarly applied to a waveform 84 showing the fluctuation of the pulse period at the second end, to produce an average curve 88. A difference 84A between the average curve 88 and the waveform 84 forms a graph. Similar to the difference 82A, the difference 84A is a fluctuation component which is taken into consideration in the present embodiment.

The template (refer to reference numeral 82A) is consecutively compared against the graph (refer to reference numeral 84A). When a portion which matches the template is found, a time difference dt1 is identified. The time difference dt1 is the propagation time of the blood. According to the method of FIG. 8, even when there is a change with respect to time of a longer period, the influence thereof may be reduced. That is, the calculation precision of the propagation time can be improved.

The invention claimed is:

1. An ultrasound diagnostic apparatus comprising:
a memory coupled to a processor, the memory storing instructions that when executed by the processor, configured the processor to:
produce, based on data acquired by transmission and reception of ultrasound, a template which represents a fluctuation of a pulse at a first end of a blood vessel of interest running in a tissue of interest,
produce, based on the data, a graph which represents a fluctuation of a pulse at a second end of the blood vessel of interest, the graph having time as a first axis and a pulse period as a second axis,
determine a portion of a period of a pulse period of the graph that is a match with the template when a correlation value satisfies a predetermined condition,
calculate a propagation time of blood between the first end and the second end based on a time difference between a first time in a center of the template and a second time in a center of the portion of the graph having the match, and
estimate a length of the tissue of interest based on the propagation time of the blood.

2. The ultrasound diagnostic apparatus according to claim 1,
wherein the tissue of interest is an umbilical cord, and
wherein the processor is configured to estimate a length of the umbilical cord as the length of the tissue of interest.

3. The ultrasound diagnostic apparatus according to claim 1,
wherein the processor is configured to estimate the length of the tissue of interest by multiplying the propagation time of the blood by an average velocity of the blood.

4. The ultrasound diagnostic apparatus according to claim 3,
wherein processor is configured to calculate the average velocity of the blood based on Doppler information included in the data.

5. The ultrasound diagnostic apparatus according to claim 3,
wherein the average velocity of the blood is designated by a user or is identified based on fetus information.

6. The ultrasound diagnostic apparatus according to claim 1, further comprising:
an image former that forms an ultrasonic image based on the data,
wherein the processor is configured to produce the template based on a change with respect to time of brightness information at the first end in the ultrasonic image, and
produce the graph based on a change with respect to time of brightness information at the second end in the ultrasonic image.

7. The ultrasound diagnostic apparatus according to claim 6,
wherein a first region of interest is set on the ultrasonic image, including the first end and for observing the change with respect to time of the brightness information at the first end, and
wherein a second region of interest is set on the ultrasonic image, including the second end and for observing the change with respect to time of the brightness information at the second end.

8. A method of measuring a length of an umbilical cord, the method comprising:
producing, based on data acquired by transmission and reception of ultrasound, a template which represents a fluctuation of a pulse at an upstream-side end of a blood vessel of interest running in an umbilical cord;
producing, based on the data, a graph which represents a fluctuation of a pulse at a downstream-side end of the blood vessel of interest, the graph having time as a first axis and a pulse period as a second axis;
determining a portion of a period of a pulse period of the graph that is a match with the template when a correlation value satisfies a predetermined condition;
calculating a propagation time of blood from the upstream-side end to the downstream-side based on a time difference between a first time in a center of the template and a second time in a center of the portion of the graph having the match; and
estimating a length of the umbilical cord based on the propagation time of the blood.

9. The method of measuring the length of the umbilical cord according to claim 8,
wherein the blood vessel of interest is an artery,
wherein the upstream-side end is located inside or near a fetus, and
wherein the downstream-side end is located inside or near a placenta.

10. The method of measuring the length of the umbilical cord according to claim 8,
wherein the blood vessel of interest is a vein,
wherein the upstream-side end is located inside or near a placenta, and
wherein the downstream-side end is located inside or near a fetus.

11. A non-transitory recording medium storing a program executed by an information processor, wherein the program, when executed by the information processor, configures the information processor to execute functions comprising:

producing, based on data acquired by transmission and reception of ultrasound to and from a mother, a template which represents a change with respect to time of an upstream-side end of a blood vessel of interest running in an umbilical cord;

producing, based on the data, a graph which represents a change with respect to time of a downstream-side end of the blood vessel of interest, the graph having time as a first axis and a pulse period as a second axis;

determining a portion of a period of a pulse period of the graph that is a match with the template when a correlation value satisfies a predetermined condition;

calculating a propagation time of blood from the upstream-side end to the downstream-side end based on a time difference between a first time in a center of the template and a second time in a center of the portion of the graph having the match; and estimating a length of the tissue of interest based on the propagation time of the blood.

\* \* \* \* \*